United States Patent
Andersson et al.

(10) Patent No.: US 7,078,040 B2
(45) Date of Patent: Jul. 18, 2006

(54) METHOD OF INHIBITING THE EXPRESSION OF INFLAMMATORY CYTOKINES AND CHEMOKINES

(75) Inventors: Tove Andersson, Stockholm (SE); Sven Pettersson, Tullinge (SE)

(73) Assignee: Fuji Chemical Industry Co., Ltd., Toyama-Pref (JP)

( * ) Notice: Subject to any disclaimer, the term of this patent is extended or adjusted under 35 U.S.C. 154(b) by 243 days.

(21) Appl. No.: 10/239,192

(22) PCT Filed: Mar. 21, 2001

(86) PCT No.: PCT/SE01/00600

§ 371 (c)(1),
(2), (4) Date: Sep. 27, 2002

(87) PCT Pub. No.: WO01/72296

PCT Pub. Date: Oct. 4, 2001

(65) Prior Publication Data

US 2003/0078304 A1    Apr. 24, 2003

(30) Foreign Application Priority Data

Mar. 27, 2000  (SE) .................................. 0001071

(51) Int. Cl.
*A61K 36/02*    (2006.01)

(52) U.S. Cl. .................................. 424/195.17; 514/725
(58) Field of Classification Search ............ 424/195.17
See application file for complete search history.

(56) References Cited

U.S. PATENT DOCUMENTS

| | | | |
|---|---|---|---|
| 3,920,834 A * | 11/1975 | Klaui et al. .................. | 514/547 |
| 5,527,533 A | 6/1996 | Tso et al. | |
| 5,712,311 A * | 1/1998 | Soudant et al. ............. | 514/572 |
| 5,886,053 A | 3/1999 | Schmutzler et al. | |
| 6,344,214 B1 * | 2/2002 | Lorenz ....................... | 424/451 |

FOREIGN PATENT DOCUMENTS

| | | |
|---|---|---|
| EP | 0 770 385 A1 * | 5/1997 |
| WO | WO 9837874 A1 | 9/1998 |
| WO | WO 9845241 A2 | 9/1998 |
| WO | WO 9911251 A1 | 3/1999 |

OTHER PUBLICATIONS www.copewithcytokines.de/cope.cgi?5231; accessed Dec. 13, 2004.*
Savoure et al. (International Journal for Vitamin and Nutritrion Research (1995), vol. 65, No. 2, pp. 79-86).*
Physiol. Chem. Phys. & Med. NMR., vol. 22, 1990, Michi Kurashige et al., "Inhibition of Oxidative Injury of Biological Membranes by Astaxanthin", p. 27-p. 38, pp. 35-37, 30.
STN International, file CAPLUS, CAPLUS accession No. 1986:85415, document No. 104:85415, Popova, N.V. et al., "Carotenoids of the fruit of *Capsicum annuum*"; & Farm. Zh. (Kiev) (1985), (6), 50-4, lines 13-26.
Patent Abstracts of Japan, abstract of JP 7-99924 A (nippon suisan kasha ltd), Apr. 18, 1995.
Patent Abstracts of Japan, abstract of JP 7-300421 A (Itano Reitou KK), Nov. 14, 1995.

* cited by examiner

*Primary Examiner*—Susan D. Coe
(74) *Attorney, Agent, or Firm*—Bacon & Thomas, PLLC

(57) ABSTRACT

A method of inhibiting the expression of inflammatory cytokines and chemokines in an animal or man, is disclosed. The method comprises administration to said animal or man of at least one type of xanthophyll, e.g. astaxanthin, in an amount inhibiting the expression of inflammatory cytokines and chemokines in said animal or man. Use of at least one type of xanthophyll, such as astaxanthin, for the preparation of a medicament for the prophylactic and/or therapeutic inhibition of the expression of inflammatory cytokines and chemokines in an animal or man, is described. Further, a commercial package containing a medicament comprising at least one type of xanthophyll, e.g. astaxanthin, and written and/or data carrier instructions for administration to an animal or man of the medicament for the prophylactic and/or therapeutic inhibition of the express of inflammatory cytokines and chemokines, is disclosed.

5 Claims, 1 Drawing Sheet

METHOD OF INHIBITING THE EXPRESSION OF INFLAMMATORY CYTOKINES AND CHEMOKINES

The present invention relates to a method of inhibiting the expression of inflammatory cytokines and chemokines in an animal or man, and to the use of a xanthophyll, e.g. astaxanthin, for the preparation of a medicament for the prophylactic and/or therapeutic inhibition of the expression of inflammatory cytokines and chemokines.

BACKGROUND

The nuclear factor-κB (NF-κB) is a conditionally regulated transcription factor that plays a key role in the expression of a variety of genes involved in inflammation, cell survival, apoptosis, cell differentiation and cancer. It was first identified as a regulator of κ light chain expression in murine B-lymphocytes, but has now been shown to be expressed ubiquitously and to be a master regulator of several important processes. The NF-κB family consists of structurally related proteins of the Rel family, including p50, p52, p65/RelA, c-Rel and RelB (reviewed in Rothwarf and Karin, 1999). In unstimulated cells, NF-κB is bound to the inhibitor protein IκB, which masks the nuclear localisation signal of NF-κB and retains it in the cytoplasm. Activation of the cell with various stimuli initiates signalling pathways involving activation of a whole series of protein kinases. This results in phosphorylation of IκB, targeting the protein for degradation (Rothwarf and Karin, 1999). As a result, the IκB/NF-κB complex dissociates, NF-κB translocates to the nucleus and binds to its cognate sites. Nuclear translocation of NF-κB is activated by various stimuli, including the inflammatory cytokines TNF-α and IL-1, UV-irradiation, mitogens, viruses, bacterias, double stranded DNA, ionizing radiation and hydrogen peroxide, in accordance with the important role played by NF-κB in various tissues (Rothwarf and Karin, 1999).

The functional importance of NF-κB in acute and chronic inflammation is based on its ability to regulate the promoters of a variety of genes. The products of such genes are e.g. cytokines, adhesion molecules and acute phase proteins, which are critical for inflammatory processes (Baeuerle et al., 1995, Shakov et al., 1990, Libermann et al., 1990). These findings are further underlined by the demonstration that mice containing targeted disruptions of the NF-κB subunits p50, RelB and c-Rel are compromised in various aspects of immune function and inflammatory processes (Sha et al., 1995; Weih et al., 1995, Köntgen et al.; 1995). Moreover, elevated levels of p65 have been observed in patients with rheumathoid arthritis and Inflammatory Bowel Disease (IBD). A role for NF-κB in inflammation was further established in a recent study, demonstrating that local administration of an antisense oligonucleotide targeted against the translational start site of NF-κB p65 abrogates established intestinal inflammation in mice (Neurath et al., 1996).

During the last years, it has become evident that redox regulation is an important mechanism that regulates conditional gene expression. Several transcription factors have been shown to be redox-regulated, including NF-κB. One common step in the activation mechanisms that lead to NF-κB translocation has been suggested to involve reactive oxygen species, based on the finding that NF-κB activation can be inhibited by a series of antioxidants (reviewed in Pitette et al., 1997). However, little is known about the pathways that activate and control NF-κB e.g. during oxidative stress.

Due to the involvement of the transcription factor NF-κB in inflammatory processes it could be possible to inhibit the expression of inflammatory cytokines and chemokines by affecting the function of the NF-κB in an animal or human.

DESCRIPTION OF THE INVENTION

The present invention provides a method to inhibit the expression of inflammatory cytokines and chemokines in an animal or man.

The method of the invention comprises administration to an animal or man of at least one type of xanthophyll in an amount inhibiting the expression of inflammatory cytokines and chemokines in said animal or man.

Examples of inflammatory cytokines are TNF-α and IL-1, and examples of chemokines are MIP-2, CXC 5 and CXC 6.

The daily doses of the xanthophyll for inhibiting the expression of inflammatory cytokines and chemokines will normally be in the range of 0.01 to 50 mg per kg body weight of an animal or human, but the actual dose will be decided based on the recommendations of the manufacturer of the medicament comprising the xanthophyll.

In an embodiment of the method of the invention the type of xanthophyll is astaxanthin. The astaxanthin may be selected from the group consisting of astaxanthin from a natural source, such as a culture of the alga *Haematococcus* sp., synthetic astaxanthin and mixtures thereof.

Astaxanthin from other natural sources than algae, such as from fungi and crustaceans, and other xanthophylles as well, are expected to be similarly useful for the purposes of the invention. An advantage of using astaxanthin from algae may be that the astaxanthin exists in a form esterified with fatty acids, which esterified astaxanthin thereby is more stable during handling and storage than free astaxanthin.

Another aspect of the invention is directed to the use of at least one type of xanthophyll for the preparation of a medicament for the prophylactic and/or therapeutic inhibition of the expression of inflammatory cytokines and chemokines in an animal or man.

In a preferred embodiment the type of xanthophyll is astaxanthin. The astaxanthin may be selected from the group consisting of astaxanthin from a natural source, such as a culture of the alga*Haematococcus* sp., synthetic astaxanthin and mixtures thereof.

Yet another aspect of the invention is directed to a commercial package containing a medicament comprising at least one type of xanthophyll and written and/or data carrier instructions for administration to an animal or man of the medicament for the prophylactic and/or therapeutic inhibition of the expression of inflammatory cytokines and chemokines.

The medicament preferably comprises astaxanthin, selected from the group consisting of astaxanthin from a natural source, such as a culture of the alga*Haematococcus* sp., synthetic astaxanthin and mixtures thereof.

The commercial package of the invention may additionally contain a water soluble antioxidant, such as glutathione and/or ascorbic acid (vitamin C) and/or a fat soluble antioxidant other than the xanthophyll, such as tocopherol (vitamin E).

The commercial package and/or the medicament comprised by the present invention may comprise additional ingredients which are pharmacologically acceptable inactive or active in prophylactic and/or therapeutic use, such as excipients and flavouring agents.

EXPERIMENTS

Figure 1:
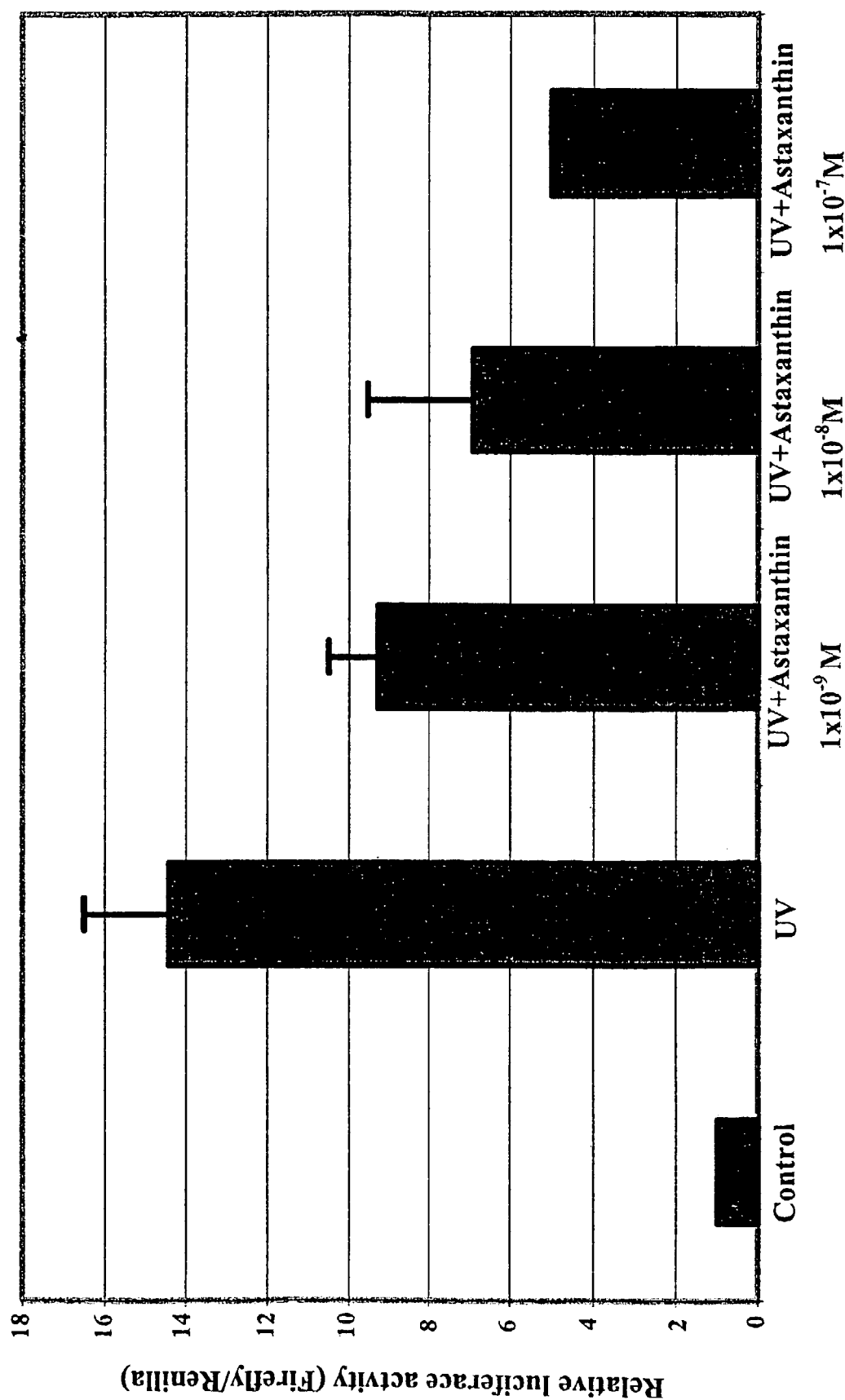
FIG. 1 is a diagram which shows that Astaxanthin inhibits the activation of NF-κB effected by UV exposure. HeLa cells were transfected with a NF-κB-dependent reporter gene and exposed to UV-C 24 hours after transfection. Pretreatment with Astaxanthin was done 3 hours prior to irradiation, where indicated. Cells were harvested and luciferase activity was measured 14–18 hours following exposure. The ratio between Firefly and Renilla luciferase activity is represented as fold activation over the activity in unstimulated control cells. The standard error is based on two identical experiments.

The experiments were conducted in order to show that astaxanthin inhibits the activation of NF-κB effected by UV exposure and thus the expression of inflammatory cytokines and chemokines.

MATERIALS AND METHODS

Cell culture

The human fibroblast cell line Hela Tet/off was cultured in MEM alpha medium supplemented with 10% fetal calf serum, penicillin and streptomycin (Gibco Grand Island, N.Y.). The day before transfection, cells were plated on 6 cm dishes in a medium containing 2.5% fetal calf serum. On the day of transfection, the cell culture medium was changed to fresh medium (2.5% fetal calf serum).

Preparation of Astaxanthin

A stock solution of Astaxanthin was prepared by dissolving synthetic Astaxanthin (Sigma) in 99.6% ethanol. The concentration of Astaxanthin was measured by spectrophotometry, and the absorbance maximum at 474–479 run was used to calculate the concentration, according to the formula: $Abs_{max}/210$.

Plasmids

The 6XκB-Luc plasmid contains a firefly luciferase reporter gene driven by 6 NF-κB binding sites cloned upstream of a TK promoter (Meyer et al. 1993). The pRL-TK plasmid contains a Renilla luciferase reporter gene driven by the TK promoter and is used as a control for transfection efficiency (Promega).

Transfection, UV Irradiation and Reporter Gene Analysis

Plasmid DNA (1 µg of the 6xκB-Luc reporter gene plasmid and 200 ng of pRL-TK control plasmid) was added to a mixture of 4 µl fuGENE 6 transfection reagent (Boeringer Ingelheim, Germany) and 196 µl serum free medium and incubated for 15 min at room temperature, according to the manufacturers protocol. DNA/fuGENE 6 was added to HeLa cells at 50% confluency and the cells were left in a 37° C. incubator. 24 hours after transfection, the medium was removed and cells were exposed to UV. For this, a Stratalinker 1800 (Stratagene) emitting a wavelength of 254 nm was used and 10 $J/m^2$ was applied. The same medium was then added back to the cells, and the cells were incubated at 37° C. Where indicated, cells were pretreated with Astaxanthin for 3 hours, by adding various concentrations of Astaxanthin to the medium. After addition, the Astaxanthin was left in the medium throughout the experiment.

Extracts were prepared 14–18 hours following exposure, and luciferase assays were performed using components of the luciferase assay system (Promega).

Results

To analyse whether Astaxanthin has any effect on the activation of NF-κB we performed transient transfection experiments in HeLa cells. NF-κB has been shown to be responsive to UV-irradiation (reviewed in Pitette et al., 1997). Similarly, we demonstrate that exposure of the cells to UV-C induces expression of a transfected NF-κB-dependent reporter gene (FIG. 1). Moreover, pretreatment of the cells with Astaxanthin at the highest concentration repressed this activation almost 3-fold. These data indicate that Astaxanthin has an inhibitory effect on NF-κB, DNA binding activity of NF-κB and/or translocation of the NF-κB across the nuclear membrane by interfering with at the signalling components in the NF-κB activation pathway.

REFERENCES

Rothwarf, D., M. and M. Karin (1999). The NF-κB activation pathway: A paradigm in information transfer from membrane to nucleus. Available at www.stke.org/cgi/content/full/OC_sigtrans; 1999/5/re 1.

Baeuerle, P., A. and T. Henkel. (1994). Function and activation of NF-κB in the immune system. *Annu. Rev. Immunol.* 12, 141–179.

Shakhov A., N., Collart, M., A., P., Vassalli, S., A., Nedospasov, and C., V. Jongeneel. (1990). κB-type enhancers are involved in lipopolysaccharide-mediated transcriptional activation of the tumor necrosis factor a gene in primary macrophages. *J. Exp. Med.* 171, 35–47.

Libermann, T. A and D. Baltimore. (1990) Activation of interleukin-6 gene expression through the NF-κB trasncription factor. *Mol. Cell. Biol.* 10, 237–2334.

Sha, W., C., Liou, H., C., Tuomanen, E., I. and D., T. Baltimore. (1995). Targeted disruption of the p50 subunit of NF-kappa B leads to multifocal defects in immune responses. *Cell.* 80, 321–30.

Weih, F., Carrasco, D., Durham, S. K., Barton, D., S., Rizzo, C., A., Ryseck, R., P., Lira, S., A. and R. Bravo. (1995). Multiorgan inflammation and hematopoietic abnormalities in mice with a targeted disruption of RelB, a member of the NF-kappa B/Rel family. *Cell* 80, 331–40.

Köntgen, F., Grumont R., J., Strasser A., Metcalf, D., Li, R., Tarlinton, D. and S. Gerondakis. (1995). Mice lacking the c-rel proto-oncogene exhibit defects in lymphoid proliferation, humoral immunity, and interleukin-2-expression. *Genes Dev.* 9, 1965–1977.

Neurath, M., F., Pettersson, S., Meyer zum Büschenfelde, K-H. and W. Strober. (1996). Local administration of antisense phosphorothioate oligonucleotides to the p65 subunit of NF-κB abrogates established experimental colitis in mice. *Nature Medicine.* 2, 998–1004.

Piette, J., Piret, B., Bonizzi, G., Schoonbroodt, S., Merville, M-P., Legrand-Poels, S., and V. Bours (1997). Multiple redox regulation in NF-κB transcription factor activation. *Biol. Chem.* 378, 1237–1245.

Meyer, M., Schreck, R., and P., A. Baeuerle. (1993). H2O2 and antioxidants have opposite effects on activation of NF-kappa B and AP-1 in intact cells: AP-1 as secondary antioxidant-responsive factor. *EMBO J.* 12, 2005–2015.

The invention claimed is:

1. Method of inhibiting the expression of inflammatory cytokines and chemokines in an animal or man by inhibiting the activation of NF-κB effected by UV-C exposure, which comprises oral administration to said animal or man of a medicament comprising astaxanthin as the sole active ingredient in an amount inhibiting the expression of inflammatory cytokines and chemokines in said animal or man.

2. Method according to claim 1, wherein the astaxanthin is selected from the group consisting of astaxanthin from a natural source, synthetic astaxanthin and mixtures thereof.

3. Method according to claim 2, wherein the natural source is a culture of the alga *Haematococcus* sp.

4. Method according to claim 1, wherein said amount inhibiting the expression of inflammatory cytokines and chemokines in said animal or man is 0.01–50 mg per kg body weight of said animal or man.

5. Method according to claim 1, wherein said inflammatory cytokines are TNF-α and IL-1 and said chemokines are MIP-2, CXC 5 and CXC 6.

* * * * *